United States Patent [19]
Mann et al.

[11] Patent Number: 5,766,901
[45] Date of Patent: Jun. 16, 1998

US005766901A

[54] APPARATUS AND METHOD FOR DELIVERING A NUCLEOTIDE INTO CELL NUCLEI

[75] Inventors: Michael J. Mann, Palo Alto, Calif.; Frank P. Diet, Köln, Germany; Victor J. Dzau, Los Altos Hills, Calif.; Gary H. Gibbons, Palo Alto, Calif.; Heiko Von der Leyen, Menlo Park, Calif.

[73] Assignee: The Board of Trustees of the Leland Stanford Junior University, Palo Alto, Calif.

[21] Appl. No.: 434,750

[22] Filed: May 4, 1995

[51] Int. Cl.$^6$ .................................................. C12N 15/00
[52] U.S. Cl. ................................. 435/172.3; 435/285.1; 435/286.6; 514/44
[58] Field of Search ........................ 514/44; 604/93, 604/96, 101, 264, 268, 280, 172.3, 285.1, 286.6

[56] References Cited

U.S. PATENT DOCUMENTS 5,328,470  7/1994  Nabel et al. ........................ 604/101

OTHER PUBLICATIONS

Furth et al., "Gene transfer into somatic tissues", Anal. Biocehm. 205: 365–368, 1992.

Yee et al., "Cellular uptake of intracerebroventricularly administered biotin–or digoxigenin–labelled antisense oligonucleotides in the rat", Cell. Mol. Neurobiol. 14(5):475–486, 1994.

Acsadi et al., "Direct gene transfer and expression into rat heart in vivo", New Biologist 3(1): 71–81, 1991.

Wolff et al., "Expression of maked plasmids by cultured myotubes and entry of plasmids into T tubules and caveolae of mammalian skeletal muscle", J. Cell Sci. 103: 1249–1259, 1992.

Nabel et al., "Recombinant Gene Expression in Vivo Within Endothelial Cells of the Arterial Wall", Science 244:1342–1344 (1989).

Nabel et al., "Site–Specific Gene Expression in Vivio by Direct Gene Transfer into the Arterial Wall", Science 249:1285–1288 (1990).

Barinaga, M. Science, vol. 266, p. 1326, 1994.
Marshall, E. Science, vol. 269, pp. 1050–1055, 1995.
Crystal, R. G. Science, vol. 270, pp. 404–410, 1995.

Orkin, S.H. et al. Report and Recommendations of the Panel to Assess the NIH Investment in Research on Gene Therapy, 1995.

Schofield, J.P. et al. British Medical Bulletin, vol. 51 (1), pp. 56–71, 1995.

Ledley, F.D. Current Opinion in Biotechnology, vol. 5, pp. 626–636, 1994.

*Primary Examiner*—James Ketter
*Assistant Examiner*—Irem Yucel
*Attorney, Agent, or Firm*—Clark & Elbing LLP

[57] ABSTRACT

The invention presents a system for inducing cells in living intact tissue, in vivo or ex vivo, to accept nucleotides from their extracellular environment and to localize those nucleotides into the cells' nuclei. This system relies on the fact that, when subjected to high pressure, cells take in nucleotides and localize those nucleotides into their nuclei with a transfection rate of greater than 90% in some cases. This invention employs various techniques for placing under high pressure either cells in isolated tissue cultures, or cells in tissues still connected to a living body. Such pressurization techniques include enclosing the tissue in an impermeable and inelastic sheath and injecting fluid into the tissue until a sufficiently high pressure is reached; placing a tissue culture in a dish and placing the dish in a pressurized chamber; mechanical pressurization techniques such as compression of a space containing fluids; occluding the ingress and egress of a vessel or organ to create a watertight compartment within the vessel or organ; and pressurization of an entire organism after delivery of nucleotide to the extracellular environment. This invention also employs various techniques for delivering a solution or suspension containing the nucleotide into the tissue; such techniques include the use of a syringe-like mechanism and a catheter.

22 Claims, 4 Drawing Sheets

APPARATUS AND METHOD FOR DELIVERING A NUCLEOTIDE INTO CELL NUCLEI

BACKGROUND—FIELD OF THE INVENTION

The present invention relates to the field of delivery of nucleotides into cells of tissues both in vivo and ex vivo, and in particular to utilizing controlled pressures to effect cell uptake and localization of exogenous nucleotides inside cell nuclei.

BACKGROUND—DESCRIPTION OF PRIOR ART

Efficient delivery of exogenous nucleotides, such as deoxyribonucleic acid (DNA), ribonucleic acid (RNA), etc., to the cells of living tissue is becoming an ever more important problem in advanced medicine and research. Free nucleotides need to be delivered into cells, both in vivo and ex vivo, for the purpose of transfection or other genetic or pharmacological manipulation. Drugs containing nucleotides have to be incorporated into cells of living tissue to be effective. In fact, for many applications, the nucleotide needs not only to be admitted into the cells, but also localized in their nuclei.

Unfortunately, no method or device is currently available to facilitate efficient delivery of exogenous nucleotides into cells of intact tissue without the use of viral vectors or liposomes. In particular, no presently known method or device ensures efficient uptake and nuclear localization of the nucleotides that are unattached to viral vectors or liposomes. Meanwhile, simple exposure of cells to DNA yields uptakes and localization in only a small percentage of cells, generally less than 5%.

The most common methods for delivering nucleotides rely on formulations, such as cationic lipids, which form complexes with DNA to facilitate the entry of DNA into cells and subsequent nuclear localization. To date, none of these formulations has been reported to achieve a transfection efficiency higher than 10% of an intact tissue either in vivo or ex vivo. In addition, exposure of living tissue to the formulations themselves is undesirable, since many of them are known to be toxic or harmful.

Another delivery method is based on DNA encapsulation. For example, in U.S. Pat. No. 4,394,448 Szoka, Jr. et al. describe a method of inserting DNA or fragments thereof into living cells. The DNA or fragment is first prepared in an aqueous mixture. This aqueous mixture is then placed in a mixture of a lipid vesicle wall-forming composition with an organic solvent. As a result, the DNA becomes encapsulated in the vesicle, and, once this has occurred, the vesicle is brought in contact with the target cell. Insertion takes place on contact. The transfection efficiency of this method and related variations is still very low.

Yet another approach to DNA delivery available for in vivo uptake is based on incorporation of the DNA into viral vectors that are then allowed to infect target cells. Although the DNA delivery rates achieved are higher than for lipid formulations, the use of viral vectors poses many risks. The vectors are potentially toxic and frequently have adverse immunologic effects, some of which are still unkown. Consequently, this method, although popular in research, has not been considered acceptable for general clinical applications, especially for use in humans.

Finally, a method taught by Sanford et al. in U.S. Pat. Nos. 5,179,022 and 5,204,253 uses accelerated microprojectiles to deliver biological material into living cells. In the first patent the microprojectiles are accelerated through a first vacuum chamber and deflected by a receiving plate into a second vacuum chamber through an aperture in the plate. In the second chamber the microprojectiles enter the biological material into which they are then incorporated. According to the second patent the microprojectiles are accelerated by a "cold" gas shock—a gas shock wave generated from an ambient temperature gas. The accelerated microprojectiles penetrate the surface of the target cells or tissues and become incorporated inside them.

This biolistic method has several drawbacks. First, it is not suited for use with intact tissues either in vivo or ex vivo due to high impact energies. Second, the microprojectiles do not easily migrate within the tissue, since they lose most of their kinetic energy on initial impact. Meanwhile, a feasible method of generating particle acceleration within tissue has not been developed.

OBJECTS AND ADVANTAGES OF THE INVENTION

In view of the above, it is the object of the present invention to provide a method and apparatus for efficient delivery of exogenous nucleotides into cells of tissues both in vivo and ex vivo. In particular, in many situations, the method and apparatus of the invention enable high delivery efficiencies with nuclear localization in more than 90% of exposed cells.

It is also an object of the invention to enable the delivery of pure nucleotides in solution, without the need for exogenous and potentially toxic substances. In particular, the invention eliminates the need for viral vectors and foreign particles or substances formerly required for the complexing of nucleotides. Also, the cells are not exposed to high-speed foreign materials, as in the case of biolistic techniques.

Yet another object of the invention is to ensure that the apparatus for delivering the nucleotides is low-cost, simple in construction, and easy to operate.

These and other objects and advantages will become more apparent after consideration of the ensuing description and the accompanying drawings.

SUMMARY OF THE INVENTION

Surprisingly, it has been found that living cells in intact tissue placed under pressure in the presence of an extracellular nucleotide will take up and localize this nucleotide in their cell nuclei. The nucleotide delivery system according to this invention therefore subjects cells in a tissue to a high-pressure fluid environment containing nucleotides. The invention employs various different systems for delivering the solution and for pressurizing the tissue. In some embodiments, the delivery system and pressurization system are the same system; this is accomplished by using a syringe-like tool to inject a nucleotide solution into a tissue. In other embodiments, the pressurization system is a gas chamber or a mechanical vise, and the delivery system is a catheter with balloons mounted on it to occlude vessels and create watertight segments within a vessel.

This nucleotide delivery system operates on any tissue which can be temporarily sealed, including entire organs or organisms. In many of the embodiments, the tissue is protected from barotrauma by the use of an impermeable, inelastic sheath surrounding it. In other embodiments, the tissue may not experience barotrauma, and it is sufficient to seal it from the passing of fluids. If the tissue is a vessel or an organ with a lumen which is already a contained space, then only the points of fluid ingress and egress need to be sealed, with balloons or temporary ligatures (such as tie-wraps).

DETAILED DESCRIPTION OF THE INVENTION

Figure 1:
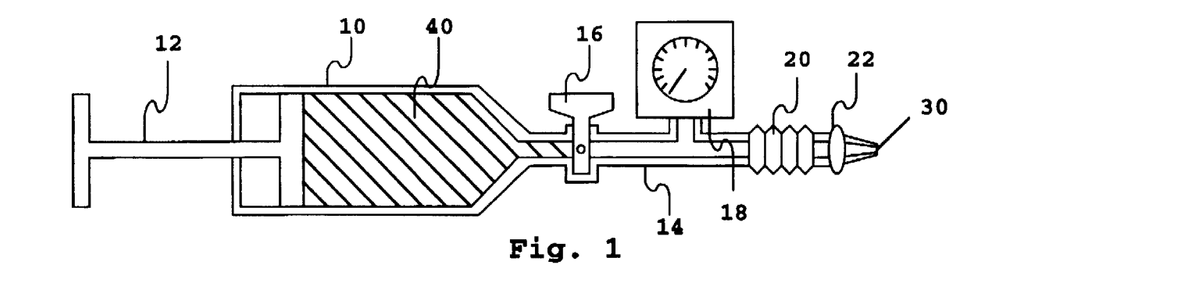
FIG. 1 depicts the preferred embodiment of the invention in the initial state.

FIG. 1 is a side view showing the initial state of the preferred embodiment of the nucleotide solution delivery system. In this embodiment, the system comprises a syringe-like structure with a reservoir 10 to hold a nucleotide solution 40, and a plunger 12. A nucleotide solution can contain DNA, RNA or associated molecules. Opposite plunger 12, reservoir 10 opens into a tube 14. Attached around tube 14, listed in order of proximity to reservoir 10, are a stopcock 16, a pressure gauge 18, a retracted sheath 20, and a notch 22. Notch 22 is next to the distal open end 30 of tube 14. Sheath 20 is neither permeable nor elastic, in order to protect the tissue from experiencing barotrauma. Stopcock 16 is initially in the closed position, preventing solution 40 from passing from reservoir 10 to tube 14.

Figure 2:
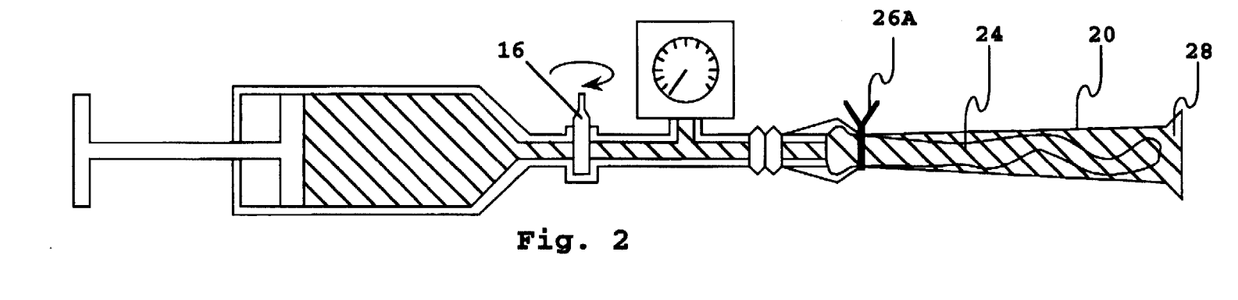
FIG. 2 depicts the nucleotide delivery system of FIG. 1 once the tissue has been mounted.

FIG. 2 illustrates how a tubular tissue sample 24 is mounted. Open end 30 is placed into the proximal end of a living, tubular tissue 24. Notch 22 fits inside proximal end of tissue 24 and a tie or ligature 26A is placed to prevent tissue 24 from slipping off open end 30. Then, sheath 20 is pulled down to cover tissue 24. Ligature 26A is wrapped around sheath 20 and tissue 24 at the point where they are attached to tube 14. In this embodiment, the ligature is a tie wrap 26A.

At this point, stopcock 16 is turned to the open position allowing nucleotide solution 40 to enter tube 14 and sheath 20, flushing out all gases and liquids present through open end 28 of sheath 20. After this flushing, a tie wrap 26B is placed over distal open end 28 of sheath 20 to form a watertight seal. In this case tie wrap 26B is placed around sheath 20 and tissue 24. Of course, it is also possible to place tie wrap 26B around sheath 20 only. One must ensure, however, that tie wrap 26B is wrapped in a tight manner.

Figure 3:
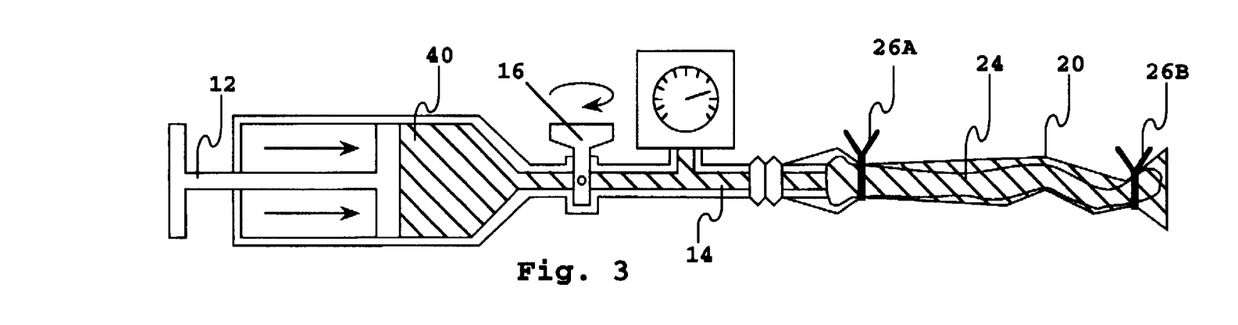
FIG. 3 depicts the nucleotide delivery system of FIG. 1 after pressurization.

FIG. 3 illustrates how nucleotide solution 40 in tissue 24 is pressurized. Stopcock 16 is turned to the open position, and plunger 12 is pushed, such that nucleotide solution 40 is injected into sheath 20 under an injection pressure. The pressure inside sheath 20 is allowed to increase until a predetermined incubation pressure—generally between at least 300 mm Hg and 1,500 mm Hg—has been reached. At this time stopcock 16 is closed (not illustrated). Tissue 24 is then allowed to incubate for a period of time, after which tie wrap 26B is untied to release the pressure (not illustrated).

Figure 4:
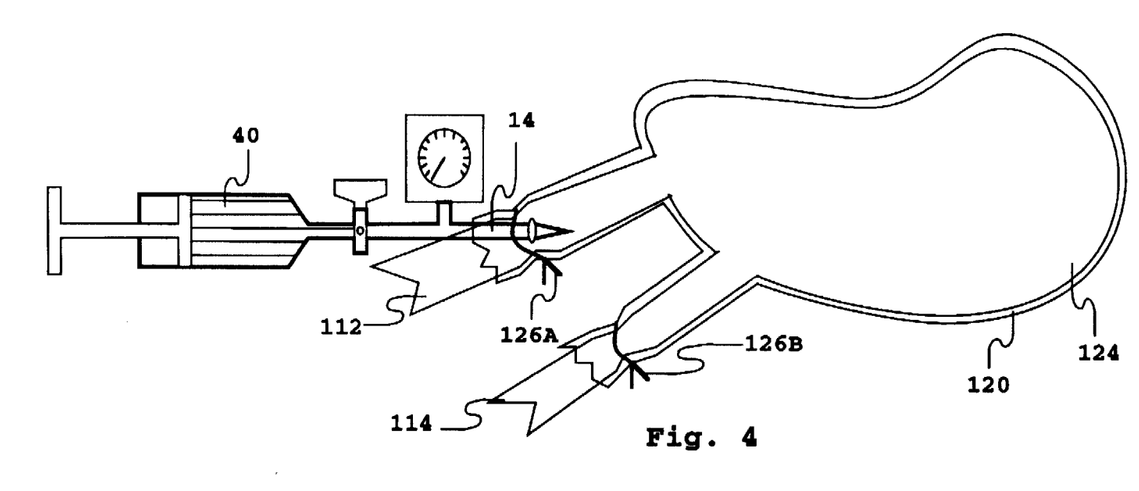
FIG. 4 depicts an alternative embodiment which operates on an entire organ.

FIG. 4 illustrates an alternative embodiment of the nucleotide delivery system which operates on an organ. In this embodiment, a protective sheath 120 is wrapped around an organ 124. Organ 124 has an artery 112 which carries blood into it and a vein 114 which carries blood away. First, tube 14 is inserted into the lumen of artery 112. Then, sheath 120 is wrapped around artery 112 and vein 114. Tie wrap 126A is tightened around sheath 120 at artery 112, and tie wrap 126B is tightened around sheath 120 at vein 114, to prevent leakage of fluid out of organ 124. Tie wrap 126A allows tube 14 to enter artery 112, yet wraps tightly enough to seal artery 112 from leakage. At this point, nucleotide solution 40 is injected, and organ 124 is allowed to incubate. After the incubation period, tie wraps 126A and 126B are removed, and blood is allowed to flow through organ 124 once more. Other than these differences, this embodiment is identical in structure and operation with the preferred embodiment.

Figure 5:
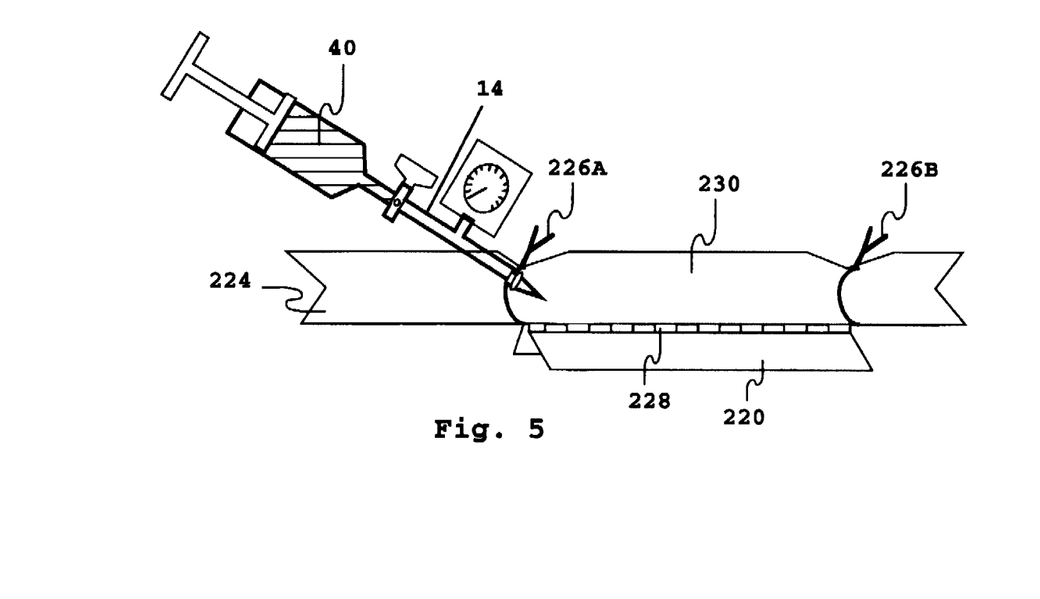
FIG. 5 depicts an alternative embodiment which operates on a segment of tubular tissue still connected to a vessel.

FIG. 5 illustrates an alternative embodiment which operates on a segment of tubular tissue, for example, a blood vessel. In this embodiment, tube 14 is inserted into the lumen of a vessel 224 which is still connected to the body of a living animal. A sheathing sheet 220 wraps around vessel 224, and a fastener 228 attaches the two flaps of sheet 220 to form a tube. In this embodiment, fastener 228 may be a heat seal. Two tie wraps 226A and 226B wrap around sheet 220. Tie wrap 226A wraps around sheet 220 where tube 14 enters, and tie wrap 226B wraps around the other end of sheet 220. Tie wraps 226A and 226B thus make a segment 230 of vessel 224 watertight. At this point, nucleotide solution 40 is injected, and segment 230 is allowed to incubate. After the incubation period, tie wraps 226A and 226B are removed, and segment 230 is perfused by blood once more. Other than these differences, this embodiment is identical in structure and operation with the preferred embodiment.

Figure 6:
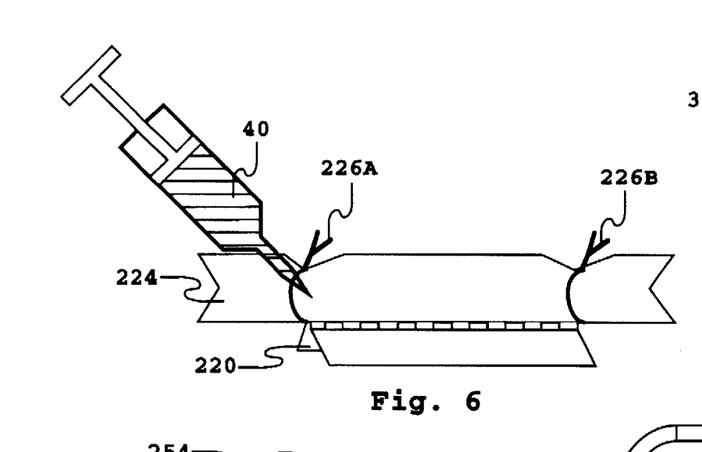
FIG. 6 depicts an alternative embodiment suited for pressurization using a mechanical pressurizing means.
Figure 7:
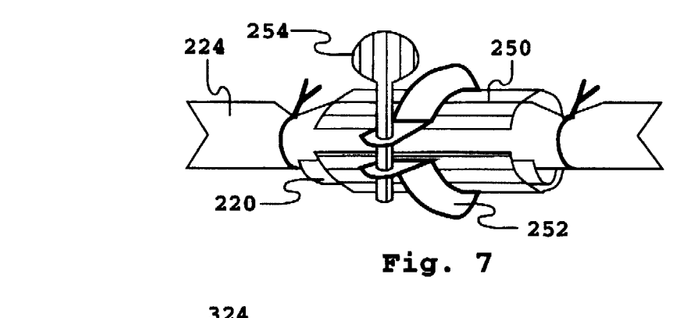
FIG. 7 depicts the embodiment of FIG. 6 after pressurization.

FIG. 6 is an alternative embodiment of FIG. 5 in which there are distinct delivery and pressurization systems. In FIG. 6, nucleotide solution 40 is delivered into the lumen of vessel 224 in the same way. But after tie wraps 226A and 226B are placed on sheet 220, a rigid tubular wrap 250 is placed around sheet 220, and a vise 252 is placed around wrap 250, as illustrated in FIG. 7. Wrap 250 is circumferentially flexible, so that the diameter of the tube it forms is variable, but it is rigid axially, so that even when its diameter changes, it still remains substantially tubular. A tightening screw 254 tightens vise 252, pulling wrap 250 tight, creating pressure within vessel 224. This pressure is maintained for an incubation period, after which screw 254 is unscrewed, releasing the pressure. Other than these differences, this embodiment is identical in structure and operation with the embodiment of FIG. 5.

Figure 8:
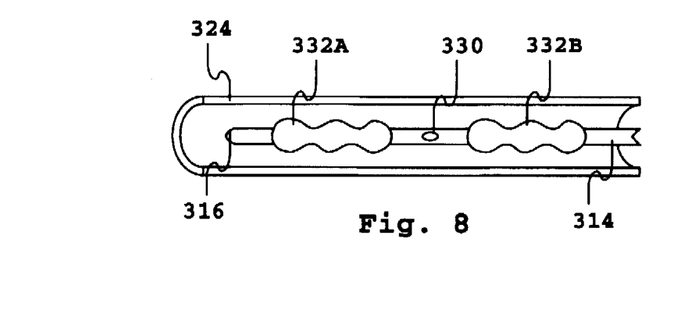
FIG. 8 depicts an alternative embodiment which uses a catheter in combination with two balloons to deliver the nucleotide solution into the lumen of a vessel.

FIG. 8 shows an alternative embodiment of the invention in which the nucleotide solution is delivered into the lumen of a vessel via a catheter. A catheter 314 is inserted into a vessel 324. Catheter 314 is closed at its end 316. Some distance from end 316, there is an open port 330. Mounted on catheter 314 before and after port 330 are two balloons 332A and 332B. Initially, balloons 332A and 332B are deflated.

Figure 9:
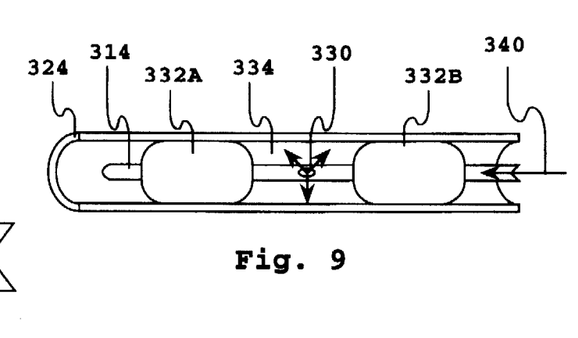
FIG. 9 depicts the embodiment of FIG. 8 after the balloons have been inflated.

FIG. 9 shows the embodiment of FIG. 8 in action. Balloons 332A and 332B are inflated, and they occlude vessel 324 where they are inflated, creating a leak-proof segment 334 within vessel 324. Then, a nucleotide solution 340 is delivered through catheter 314, exiting from port 330. Solution 340 is pressurized, so segment 334 also becomes pressurized. After an incubation period, balloons 332A and 332B are deflated and segment 334 becomes depressurized again.

Figure 10:
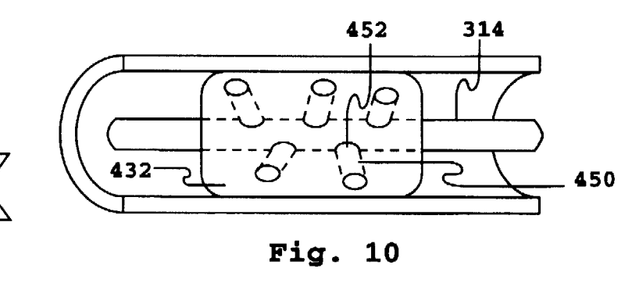
FIG. 10 depicts an alternative embodiment of FIG. 8 in which the balloons have inner tubules for delivering nucleotide solution to the walls of a vessel.

FIG. 10 shows an alternative embodiment of FIG. 8 in which a balloon mounted to the catheter has miniature tubules for delivering the nucleotide solution to the walls of the vessel. FIG. 10 shows this embodiment in the state in which a balloon 432 has already been inflated, but the nucleotide solution has not yet been delivered. In this embodiment, there is no port 330 on catheter 314. Balloon 432 has tubules 450 which are directly connected to holes 452 in the segment of catheter 314 within balloon 432.

Figure 11:
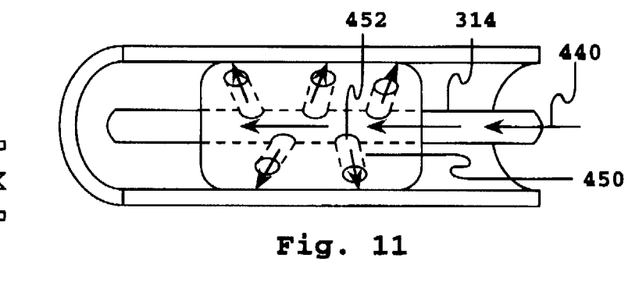
FIG. 11 depicts the embodiment of FIG. 10 with arrows showing the flow of the nucleotide solution as it is delivered.

FIG. 11 shows the embodiment of FIG. 10 in action. When a pressurized nucleotide solution 440 is delivered through catheter 314, solution 440 exits holes 452, travels through tubules 450, and reaches the walls of vessel 324. Other than these differences, this embodiment is identical to the embodiment in FIG. 8.

Figures 12, 13, 14, 15:
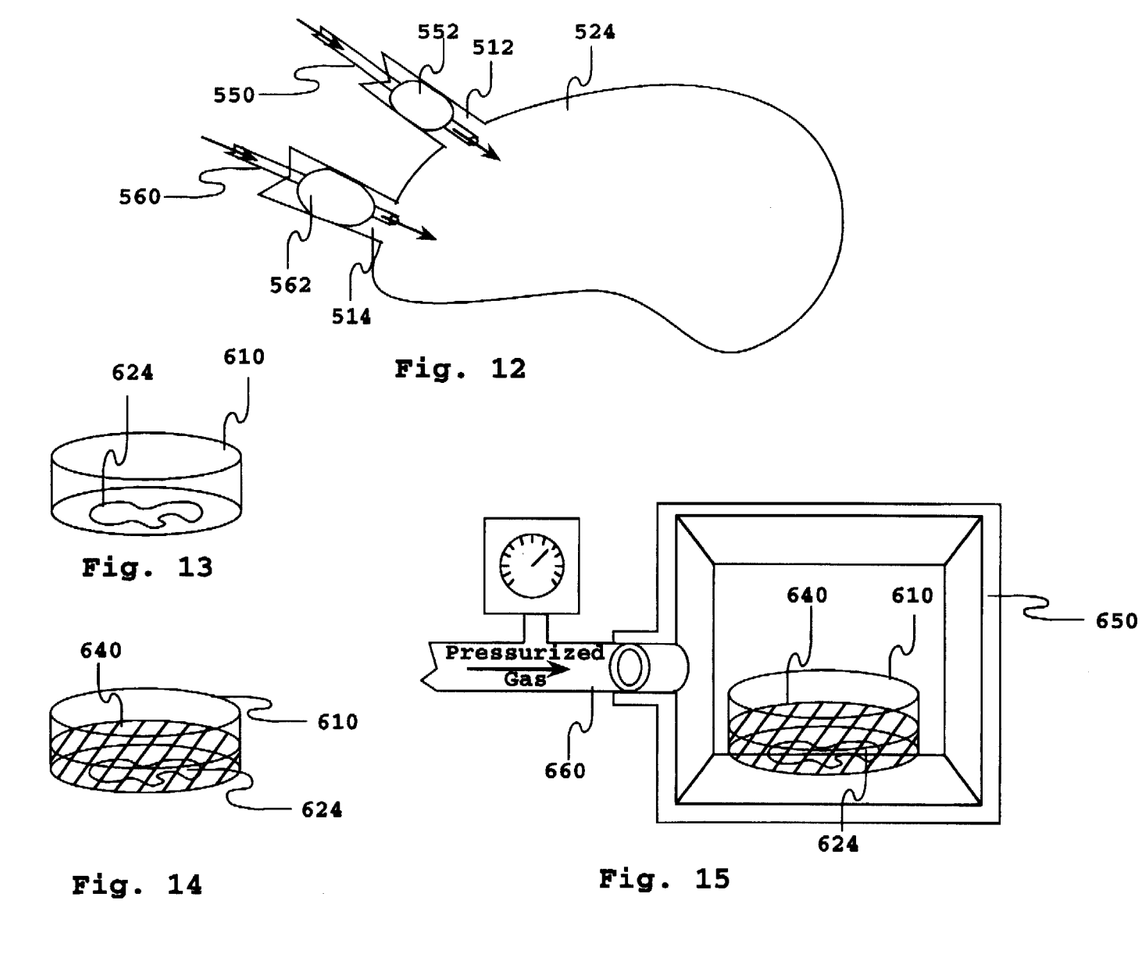
FIG. 12 depicts an alternative embodiment in which two catheters with balloons are used to pressurize an organ.
FIG. 13 depicts an alternative embodiment which operates on isolated tissue or cell cultures.
FIG. 14 depicts the embodiment of FIG. 13 after the nucleotide solution is introduced to the culture.
FIG. 15 depicts the embodiment of FIG. 13 when the culture is placed in a pressurized chamber.

FIG. 12 shows another alternative embodiment of FIG. 8 in which two catheters with balloons pressurize an organ. A catheter 550 with a balloon 552 is inserted into an artery 512 leading to an organ 524, and another catheter 560 with a balloon 562 is inserted into a vein 514 leading away from organ 524. Initially balloons 552 and 562 are deflated (not illustrated). Once their respective catheters are inserted, they are inflated, thus occluding artery 512 and vein 514. At this point, a pressurized nucleotide solution is delivered into organ 524. Other than these differences, this embodiment is identical in operation to the embodiment of FIG. 8.

FIG. 13 illustrates another alternative embodiment of the invention, which utilizes a pressure chamber. In FIG. 13, a dish 610 contains a culture 624 of living tissue. FIG. 14 shows how an unpressurized nucleotide solution 640 is introduced into culture 624. After this, dish 610 is placed into a pressure chamber 650, as shown in FIG. 15. Chamber 650 is as yet unpressurized. Then, chamber 650 is closed and sealed, and a pressurized gas, such as $CO_2$, is introduced into chamber 650 through a duct 660, thus pressurizing solution 640 and culture 624. After an incubation period, duct 660 is open to release the pressure. This embodiment can also be used for introducing a nucleotide into the cells of an entire organism. To do this an organism is placed inside chamber 650 and pressurized gas is introduced through duct 660.

From the previous descriptions, it can be seen that our nucleotide delivery system introduces exogenous nucleotides into cells in intact tissue in vivo or ex vivo without using foreign and potentially toxic substances. Specifically, this method allows cells to absorb pure DNA in solution at a 90% transfection efficiency, in some circumstances, without disrupting the normal functioning of the tissue. Furthermore, every embodiment described above uses tools and methods which are commonly available, and easy to operate.

SUMMARY, RAMIFICATIONS, AND SCOPE

Although the above descriptions contain many specificities, these should not be construed as limitations on the scope of the invention, but rather as illustrations of particular embodiments thereof. Many other variations are possible. For example, the tie wrap may be replaced by any sealing mechanism, for example, a suture ligature, a suture tie, or a clamp; the tissue need not be tubular, but only needs to be easily wrapped by a sheath; the sheath is not always necessary, for example if the tissue can maintain high pressure without a sheath. The sheath is useful for allowing exposure of the tissue to nucleotide at high pressure without over-distension of the tissue, and for preventing loss of pressure due to leakage of nucleotide solution through small holes or side branches of the tissue. Sheaths of various sizes, shapes, and materials can be used. Furthermore, a sheath may be elastic, so that it may be constricted in order to provide pressure to the tissue. An inelastic can be constricted as well, e.g., by twisting, to thus increase the pressure within. Furthermore, it is not necessary for the sheath to be in contact the tissue; a fluid solution can be introduced between the sheath and the tissue.

The system is capable of delivering nucleotides into the cells within an intact organism, provided the organism can be placed in a pressurized environment.

Furthermore, the nucleotide can be presented in either a solution or a suspension. The plunger can be automated by a servo-mechanism so as to deliver nucleotide solution at a safe but efficient rate. Another means of pressurizing tissue is to introduce an inflatable balloon into the lumen of an organ itself. The pressure can be as little as 300 mm Hg and as much as 1500 mm Hg. Lower or higher pressures are also possible, provided the nucleotide is localized in the cell nucleus and the necessary measures are taken to prevent barotrauma.

Accordingly, the scope of the invention should be determined not by the embodiments illustrated, but by the appended claims and their legal equivalents.

We claim:

1. A method of delivering a nucleic acid molecule into a cell, said method comprising the steps of:
   contacting said cell with a nucleic acid molecule in a liquid medium;
   establishing a sealed enclosure around said cell and said liquid medium; and
   establishing in said sealed enclosure an incubation pressure sufficient to enhance uptake of said nucleic acid molecule by said cell.

2. The method of claim 1, wherein said cell is in an in vitro sample.

3. The method of claim 1, wherein said cell is in a tissue that is connected to a living mammal.

4. The method of claim 1, wherein said cell is in tissue taken from a living mammal.

5. The method of claim 1, wherein said cell is in a living mammal.

6. The method of claim 1, wherein said sealed enclosure encloses an entire mammal comprising said cell.

7. The method of claim 1, wherein said cell is in endothelial tissue.

8. The method of claim 1, wherein said cell is in cardiovascular tissue.

9. The method of claim 1, wherein said nucleic acid molecule is present in solution.

10. The method of claim 1, wherein said liquid medium is brought into contact with said cell using a catheter.

11. An apparatus for delivering a nucleic acid into a cell, said apparatus comprising:

a means for establishing a sealed enclosure enclosing said cell and an extracellular environment of said cell; and a means for establishing an incubation pressure within said sealed enclosure, for facilitating an uptake of said nucleic acid from said extracellular environment into said cell.

12. The apparatus of claim 11, wherein said means for establishing said sealed enclosure comprises a protective means for protecting said tissue from experiencing trauma.

13. The apparatus of claim 12, wherein said protective means comprises an inelastic sheath adapted to be placed around said tissue.

14. The apparatus of claim 13, wherein said sheath is impermeable, for holding a fluid in a space between said sheath and said tissue.

15. The apparatus of claim 14, further comprising a sealing means for preventing a leakage of said fluid from said space.

16. The apparatus of claim 15, further comprising a flushing means for evacuating a fluid from a space contained within a tissue prior to a delivery of said nucleic acid, wherein said tissue comprises said cell.

17. The apparatus of claim 16, wherein said flushing means comprises a pumping means for passing a flushing gas through said space.

18. The apparatus of claim 17, further comprising a means for delivering a nucleic acid to an extracellular environment of said cell.

19. The apparatus of claim 18, wherein said means for delivering said nucleic acid comprises a catheter system.

20. The apparatus of claim 19, wherein said catheter system comprises two occlusion means for defining said sealed enclosure between said two occlusion means.

21. The apparatus of claim 11, wherein said means for establishing said sealed enclosure comprises a pressurization chamber.

22. An apparatus for delivering a nucleic acid into a cell, comprising:

a means for delivering said nucleic acid to an extracellular environment of said cell; and a means for establishing an incubation pressure around said cell, thereby facilitating an uptake of said nucleic acid into said cell.

* * * * *

UNITED STATES PATENT AND TRADEMARK OFFICE
CERTIFICATE OF CORRECTION

Page 1 of 2

PATENT NO. : 5,766,901
DATED : June 16, 1998
INVENTORS : Michael J. Mann, Frank P. Diet, Victor J. Dzau, Gary H. Gibbons, and Heiko Von Der Leyen It is certified that error appears in the above-identified patent and that said Letters Patent is hereby corrected as shown below:

On the face of the patent, under "OTHER PUBLICATIONS," "Furth et al.", replace "Biocehm." with --Biochem.--;

On the face of the patent, under "OTHER PUBLICATIONS," "Wolf et al.", replace "maked plasmids" with --naked plasmids--;

Col. 1, line 17, after "tissue", add the following --without the use of viral vectors or liposomes--;

Col. 1, line 31, replace "the nucleotides" with --nucleotides--;

Col. 5, line 57, replace "open to" with --opened--;

Cols. 7-8, delete claims 11-22.

In the drawings, Sheet 4 of 4, consisting of Figs. 12-15, should be deleted, and substitute therefor the corrected Sheet 4 of 4, consisting of Figs. 12-15, as shown on the attached page.

Signed and Sealed this

Sixteenth Day of March, 1999

Attest:

Q. TODD DICKINSON

*Attesting Officer*     *Acting Commissioner of Patents and Trademarks*